United States Patent
Lohne et al.

(10) Patent No.: US 12,178,290 B2
(45) Date of Patent: Dec. 31, 2024

(54) FOOTWEAR

(71) Applicant: Actiweight Labs AS, Tromsø (NO)

(72) Inventors: Gard Mikalsen Lohne, Tromsø (NO);
Marcus Christian Sletten, Tromsø (NO)

(73) Assignee: Actiweight Labs AS, Tromsø (NO)

( * ) Notice: Subject to any disclaimer, the term of this patent is extended or adjusted under 35 U.S.C. 154(b) by 387 days.

(21) Appl. No.: 17/191,221

(22) Filed: Mar. 3, 2021

(65) Prior Publication Data
US 2021/0274879 A1 Sep. 9, 2021

(30) Foreign Application Priority Data
Mar. 3, 2020 (EP) .................................. 20160672

(51) Int. Cl.
*A43B 7/20* (2006.01)
*A61F 5/01* (2006.01)

(52) U.S. Cl.
CPC .............. *A43B 7/20* (2013.01); *A61F 5/0111* (2013.01)

(58) Field of Classification Search
CPC .... A43B 7/20; A43B 7/18; A43B 7/14; A43B 5/00; A43B 5/0125; A43B 5/4528; A61F 5/0111; A61F 5/0127; A61F 5/0585; A61F 2005/0169; A61F 13/066; A61F 5/0125; A61F 5/0113; A61F 2005/0139; A61F 2005/0165; A61F 5/00; A61F 5/01–0104; A61F 5/04; A61F 5/042; A61F 5/05841; A43C 11/165; A43C 11/1493; A61B 5/4528; A61B 1/00; A61B 7/00; A61B 7/28
(Continued)

(56) References Cited

U.S. PATENT DOCUMENTS 4,559,934 A * 12/1985 Philipp ................. A61F 5/0111
602/27
4,922,630 A 5/1990 Robinson
(Continued)

FOREIGN PATENT DOCUMENTS

DE 202016004074 U1 * 8/2016
DE 102018201019 A1 8/2018
(Continued)

OTHER PUBLICATIONS

Machine translation of BORT (DE 202016004074 U1) (Year: 2016).*
(Continued)

*Primary Examiner* — Caitlin A Carreiro
(74) *Attorney, Agent, or Firm* — Osha Bergman Watanabe & Burton LLP

(57) ABSTRACT

Footwear for rehabilitation after an ankle sprain or for preventive training to avoid an ankle sprain includes a sock body including a foot section and a leg section. The footwear further includes a leg strap device and an adjustable tensioning device connected to the leg strap device. A tensioning element is defined with a first end section, a second end section and an intermediate section between the first and second end sections, where the first end section is connected to the foot section, the second end section is connected to the adjustable tensioning device and the intermediate section is provided below, or integrated as part of, an arch section of the foot section. The adjustable tensioning device is connected to the leg strap device.

8 Claims, 8 Drawing Sheets

(58) Field of Classification Search
USPC .......... 602/5, 23, 27; 36/84, 88, 89, 91, 102, 36/140, 145, 155
See application file for complete search history.

(56) References Cited

U.S. PATENT DOCUMENTS

| | | | |
|---|---|---|---|
| 4,982,733 A | 1/1991 | Broadhurst et al. | |
| 5,088,478 A * | 2/1992 | Grim | A43B 7/20 |
| | | | 128/DIG. 20 |
| 5,094,232 A * | 3/1992 | Harris | A61F 5/0123 |
| | | | 602/27 |
| 5,330,419 A * | 7/1994 | Toronto | A61F 13/065 |
| | | | 602/65 |
| 6,126,625 A * | 10/2000 | Lundberg | A61F 5/0118 |
| | | | 602/65 |
| 7,762,974 B2 * | 7/2010 | Sindel | A61F 5/0111 |
| | | | 602/65 |
| 7,935,067 B2 * | 5/2011 | McChesney | A61F 5/0111 |
| | | | 602/26 |
| 9,266,010 B2 * | 2/2016 | Kloster | A63C 10/145 |
| 9,427,350 B1 * | 8/2016 | Clements | A61F 5/01 |
| 2008/0004558 A1 * | 1/2008 | Outred | A61F 5/0113 |
| | | | 602/23 |
| 2009/0105704 A1 | 4/2009 | Gordon, Jr. | |
| 2009/0247922 A1 * | 10/2009 | Clements | A61F 5/0127 |
| | | | 602/27 |
| 2016/0051827 A1 * | 2/2016 | Ron Edoute | A61F 7/007 |
| | | | 600/14 |
| 2016/0220409 A1 * | 8/2016 | Romo | A61F 5/013 |
| 2021/0137719 A1 * | 5/2021 | Bichler | A61F 5/0111 |
| 2021/0378355 A1 * | 12/2021 | Bichler | A61F 5/0111 |

FOREIGN PATENT DOCUMENTS

| | | | | |
|---|---|---|---|---|
| DE | 102017109877 A1 | | 11/2018 | |
| EP | 1138288 A1 * | 10/2001 | ............ | A61F 5/0111 |
| WO | 2018/209332 A1 | | 11/2018 | |

OTHER PUBLICATIONS

Extended European Search Report issued in European Application No. 20160672.0, dated Jul. 13, 2020 (7 pages).

Office Action issued in counterpart European Patent Application No. 20 160 672.0 mailed on Sep. 22, 2023 (6 pages).

* cited by examiner

FOOTWEAR

FIELD OF THE INVENTION

The present invention relates to a footwear for rehabilitation after an ankle sprain or for preventive training to avoid an ankle sprain.

BACKGROUND OF THE INVENTION

An ankle sprain is an injury where sprain occurs on one or more ligaments of the angle. A sprained ankle is also referred to as a twisted ankle or rolled ankle.

Initial treatment of an ankle sprain typically consists of protection, rest, icing, compression and elevation. Depending on the severity grade of the ankle sprain, rehabilitation over a longer period is needed, to regain strength and flexibility of the ligaments and muscles.

It is known to use orthopedic walking boots to stabilize a sprained ankle. One such walking boot is known as the AirCast® AirSelect boot (See NON-PATENT DOCUMENT 1). Another type of footwear is known as the AirCast® AirSport+which aids in ankle stabilization for moderate to severe ankle sprains and chronic instabilities (See NON-PATENT DOCUMENT 2).

It is also known footwear in the form of socks to prevent ankle injuries. One such sock for preventing ankle injury is described in WO 2019/003145. The sock has an heterogenous compression where it is stated that it prevents ankle injury without affecting the normal movement of the lower limb. In addition, it is stated that these different compression zones also avoid the formation/evolution of edema after injury.

The main purpose of the prior art above is to stabilize the ankle and to compress the ankle, and hence to protect, rest and compress the ankle. However, the above prior art does not contribute substantially in training or in regaining strength and flexibility of the ankle.

The object of the present invention is to provide a footwear for rehabilitation after an ankle sprain or for preventive training to avoid an ankle sprain. More specifically, the object is to train strength and flexibility of the ankle to prevent an ankle sprain and to help a sprained ankle to regain strength and flexibility.

RELATED ART DOCUMENTS

[NON-PATENT DOCUMENT 1] "AIRCAST AIRSELECT STANDARD," DJO Global. Web address: https://www.djoglobal.com/products/aircast/airselect-standard.
[NON-PATENT DOCUMENT 2] "AIRCAST AirSport+," DJO Global. Web address: https://www.djoglobal.com/sites/default/files/AC18-MKT00-7796-RevA-AirSport%2BBrochure_r6.pdf.

SUMMARY OF THE INVENTION

The present invention relates to a footwear for rehabilitation after an ankle sprain or for preventive training to avoid an ankle sprain, wherein the footwear comprises:
 a sock body comprising a foot section and a leg section;
 a leg strap device;
 an adjustable tensioning device connected to the leg strap device;
 a tensioning element having a first end section, a second end section and an intermediate section between the first and second end sections, where:
  the first end section is connected to the foot section;
  the second end section is connected to the adjustable tensioning device;
  the intermediate section is provided below, or integrated as part of, a sole section of the foot section;
  wherein the adjustable tensioning device is connected to the leg strap device.

In one aspect, the adjustable tensioning device provides adjustable tensioning of the tensioning element with respect to the foot section of the sock body.

In one aspect, the footwear is configured to provide an adjustable inversion force or an adjustable eversion force by adjustment of the adjustable tensioning device.

In one aspect, the tensioning element is at least partially elastic.

In one aspect, the adjustable tensioning device is connected on a medial side of the leg strap device, resulting in an adjustable inversion force by adjustment of the adjustable tensioning device.

In one aspect, the adjustable tensioning device is connected on a lateral side of the leg strap device, resulting in an adjustable eversion force by adjustment of the adjustable tensioning device.

It should be noted that the terms lateral/medial and inversion/inversion refers to positions relative to the right-side foot and left-side foot of a user of the footwear. However, as will be apparent from the above, a footwear providing an eversion force when used on a left-side foot will be providing an inversion force when used on a right-side foot and vice versa.

In one aspect, the adjustable tensioning device comprises a wire connected to the second end section of the tensioning element.

In one aspect, the wire is non-elastic.

In one aspect, the adjustable tensioning device comprises a reel-based tensioning mechanism.

In one aspect, the sock body further comprises an ankle section provided between the foot section and the leg section.

In one aspect, the foot section of the sock body is at least partially covering the metatarsal area of the foot. Consequently, the foot section of the sock body is not covering the phalanges area of the foot completely. The toes will therefore protrude out from the foot section of the sock body. Hence, it is not required to manufacture the footwear in several different sizes. Moreover, it is achieved that the footwear can be used on both a right foot and a left foot. A first footwear may be used to provide an adjustable inversion force of a right foot and an adjustable eversion force of a left foot, while a second footwear may be used to provide an adjustable inversion force of a left foot and an adjustable eversion force of a right foot. Consequently, only two versions of the footwear must be manufactured.

In one aspect, the foot section may comprise a toe section. The toe section may be elastic or adjustable, to achieve that the sock body may be used on feet with different sizes.

In one aspect, the second end section of the tensioning element is provided at, or adjacent to the ankle area of the sock body.

In one aspect, the tensioning element is provided outside of the sock body. In one aspect, the leg strap device is connected to the leg section of the sock body.

Preferably, the leg strap device is connected to the upper part of the leg section. The leg strap device may be connected to the leg section by means of a seam, a zipper, a hook and loop fasteners (Velcro), a button etc. Alternatively, the leg strap device is not connected to the leg section, the only connection is provided via the tensioning element.

In one aspect, the footwear comprises a zipper provided in the upper part of the leg section of the sock body.

By means of this zipper, it is easier for a user to put the sock body onto his ankle. In many cases, the ankle is swollen after an ankle sprain, in which case the zipper is helpful. The zipper also renders it possible to use a less elastic fabric than required if the zipper was not present.

In one aspect, the first end section is connected to the foot section on the opposite side of the adjustable tensioning device.

In one aspect, the first end section is connected to the lateral side of the foot section and the adjustable tensioning device is connected to the medial side of the leg strap device. This footwear will provide an adjustable eversion force on the foot. This footwear must be made in two different versions, one for the left foot and one for the right foot.

However, in some of the above aspects, the footwear can be used interchangeably on left/right feet. Hence, if the above right foot version is used on the left foot and the above left foot version is used on the right foot, the first end section will be connected to the lateral side of the foot section and the adjustable tensioning device will be connected to the medial side of the leg strap device. Now, the footwear will be configured to provide an adjustable inversion force on the foot.

In one aspect, the footwear further comprises a guide connected to the ankle section of the sock body for positioning the tensioning element in relation to the sock body.

DETAILED DESCRIPTION

Embodiments of the invention will now be described with reference to the enclosed drawings, where:

Figure 5:
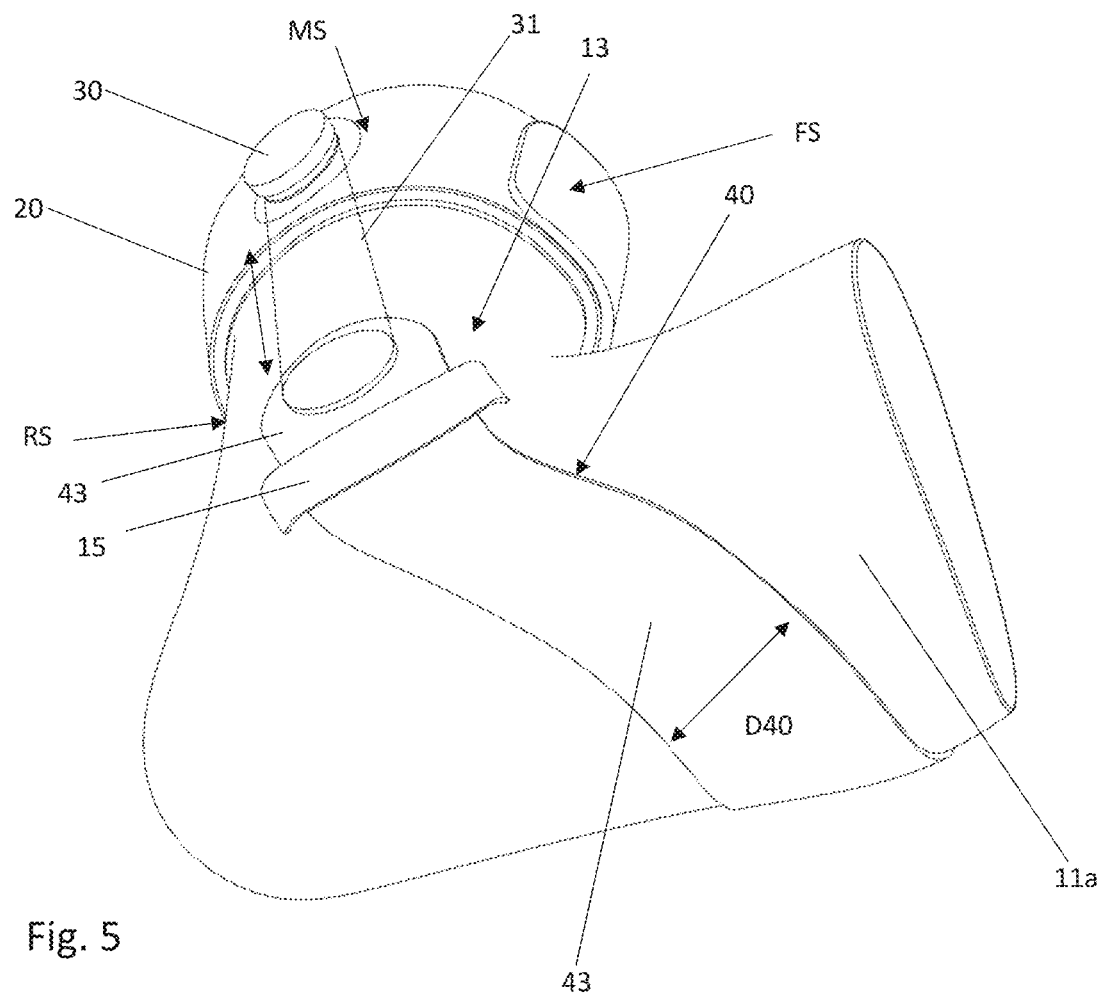
FIG. 5 illustrates a perspective bottom view of the first embodiment.
Figure 6:
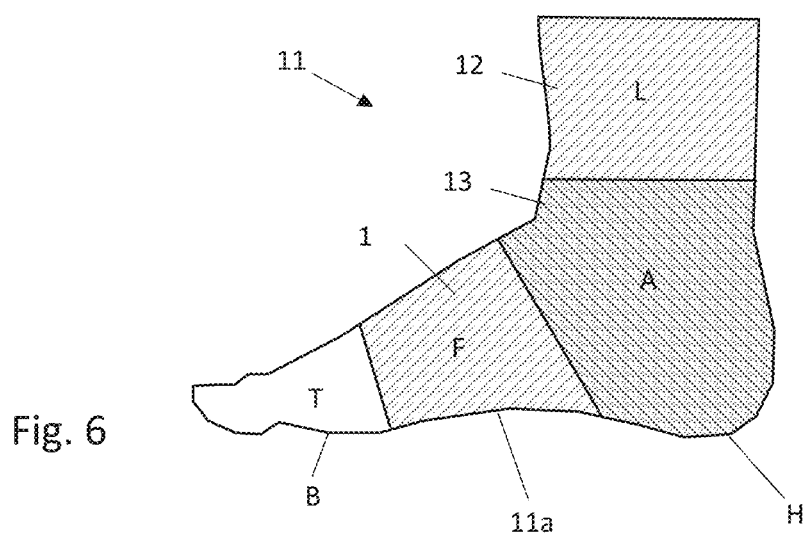
FIG. 6 illustrates the sections of the sock body and the parts of the foot.
Figure 7A:
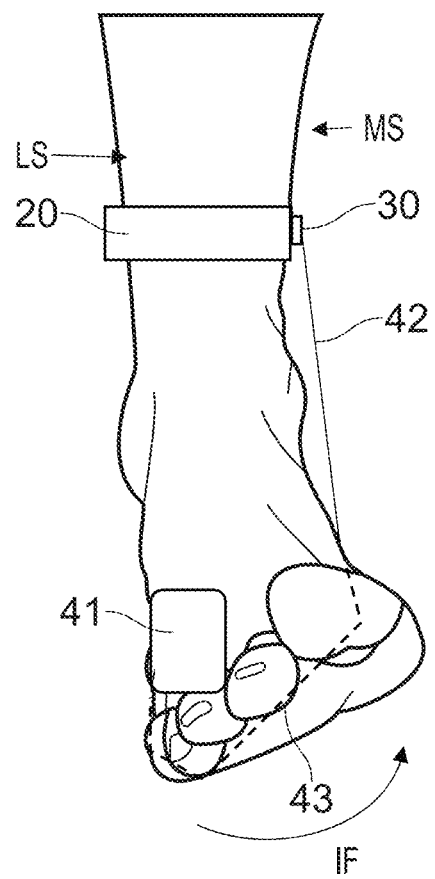
Figure 7B:
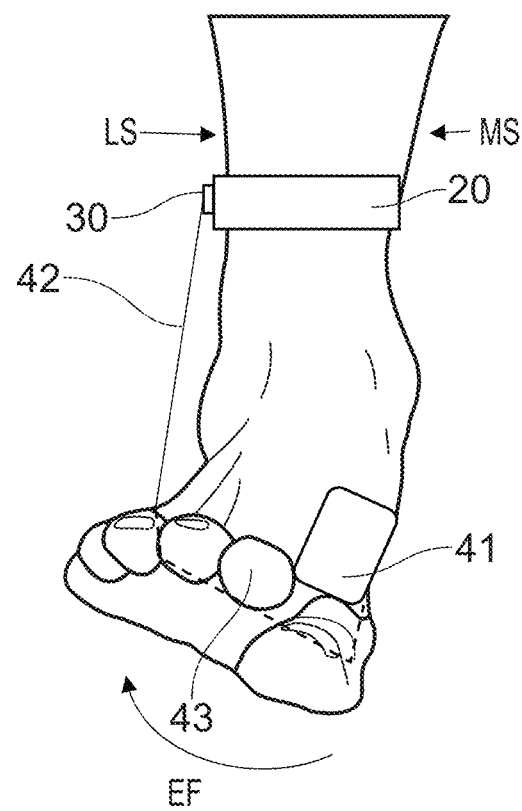
Figure 7C:
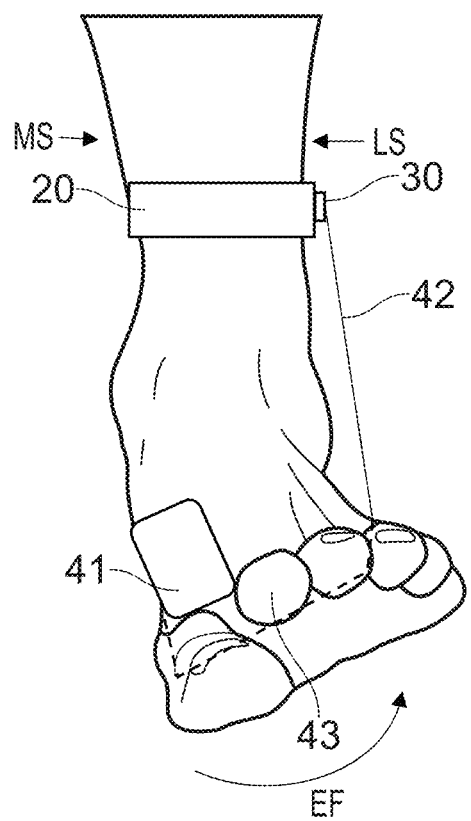
Figure 7D:
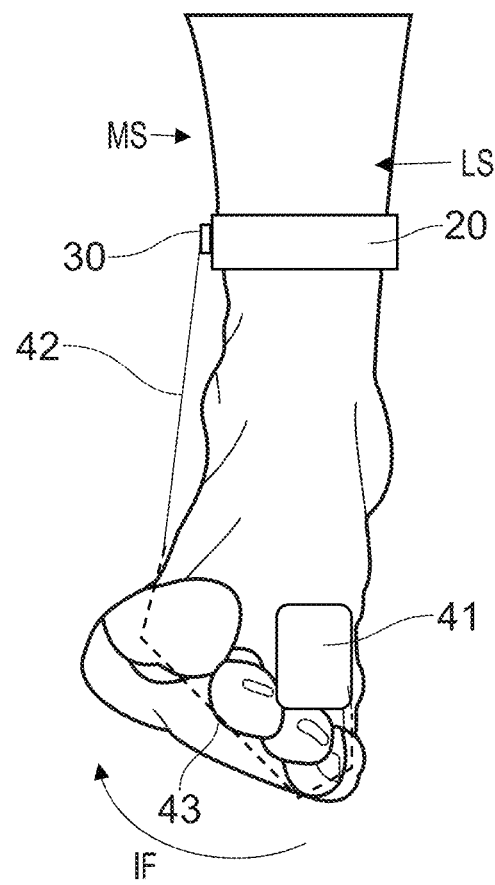
Figure 8:
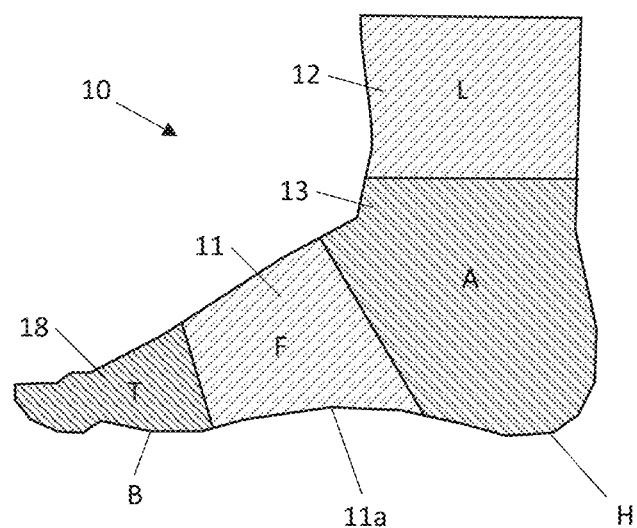
Figure 9:
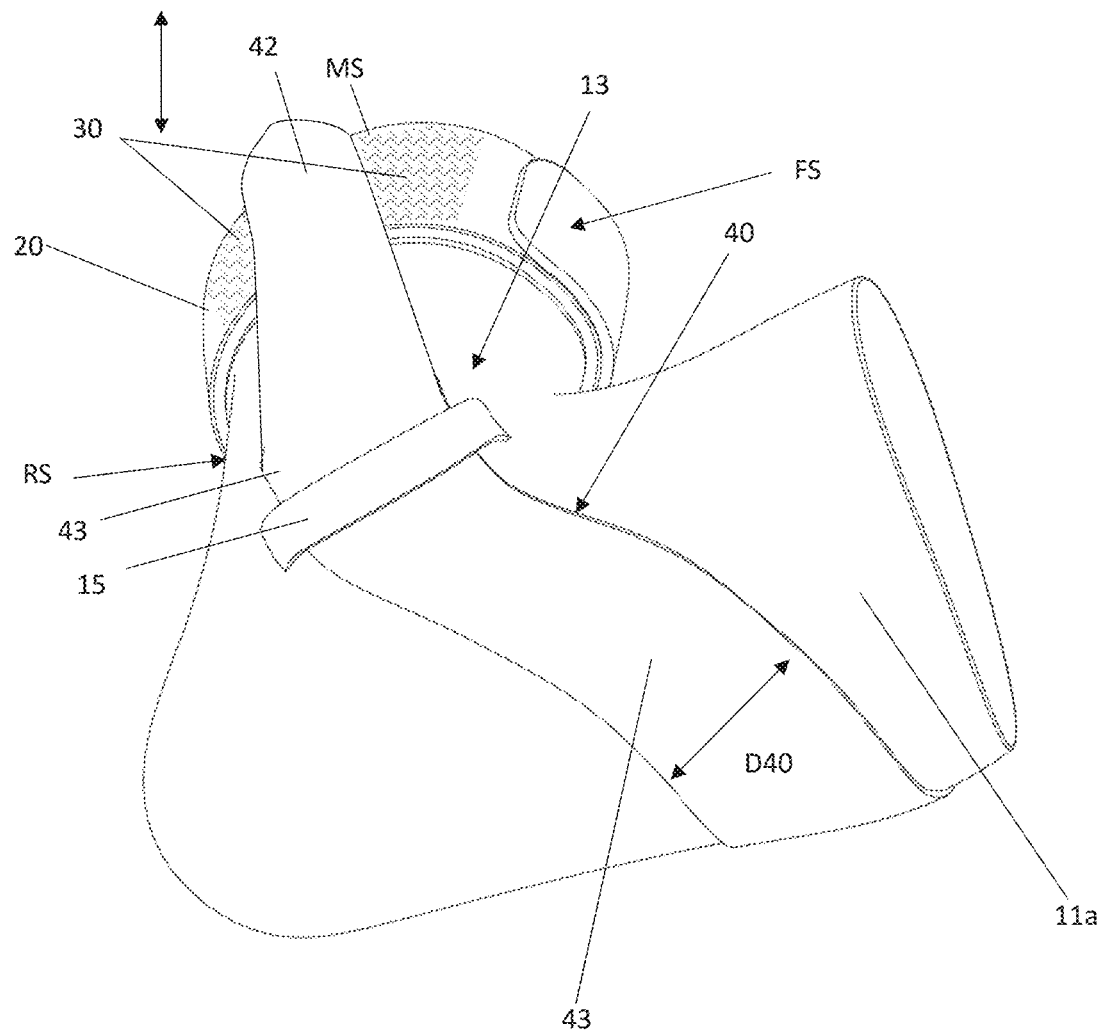

FIG. 7a-d illustrates a front view of the ankle region during inversion and eversion of a right foot and a left foot;

FIG. 8 corresponds to FIG. 6, where the sock body has a toe section;

FIG. 9 shows an alternative embodiment of FIG. 5.

Initially, the anatomy of the ankle region will be described in short with reference to FIGS. 1, 2a and 2b. The ankle region AR is the region where the foot F and the leg L meet.

The bones of the foot area F are divided into three groups. The posterior foot is formed by the seven tarsal bones, the area of these tarsal bones is shown as the tarsals area TA. The mid-foot has the five metatarsal bones, the area of these metatarsal bones is shown as the metatarsals area MTA. The toes contain the phalanges, the area of these phalanges is shown as the phalanges area PA.

Figure 1:
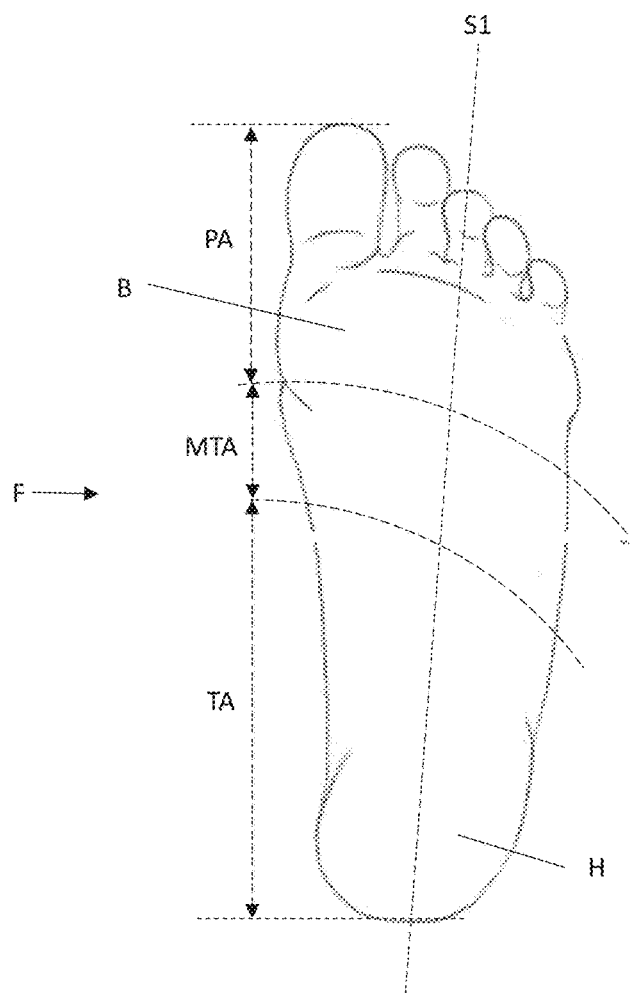
FIG. 1 illustrates the anatomy of the foot seen from below the foot (i.e. sole)
Figures 2A, 2B:
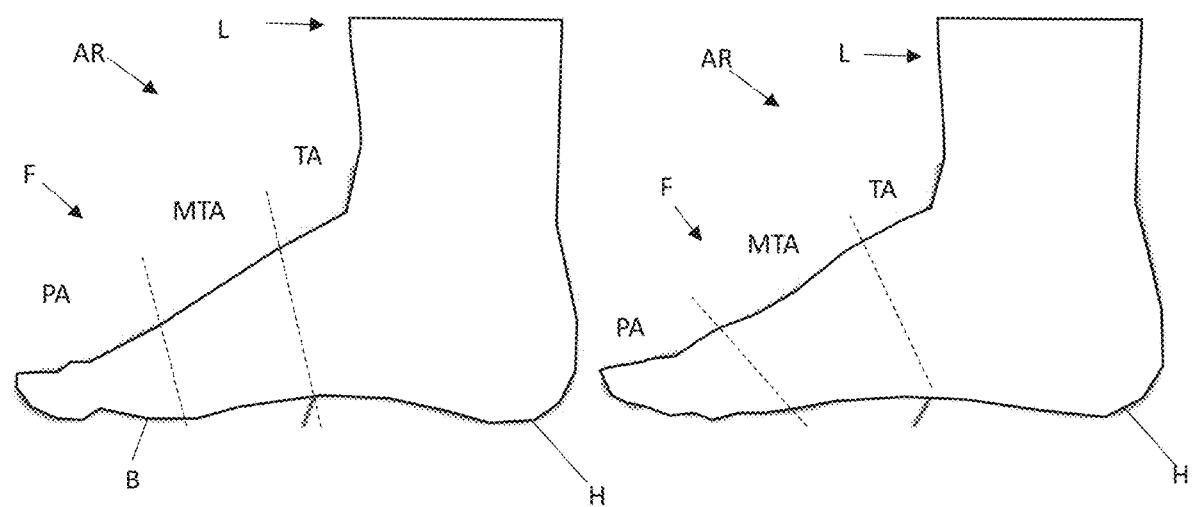
FIG. 2a illustrates a medial side view of the ankle region.
FIG. 2b illustrates a lateral side view of the ankle region.

Also the heel H, ball B, sole S of the foot is indicated in FIGS. 1, 2a and 2b, together with the longitudinal center axis SI of the sole.

Figure 2C:
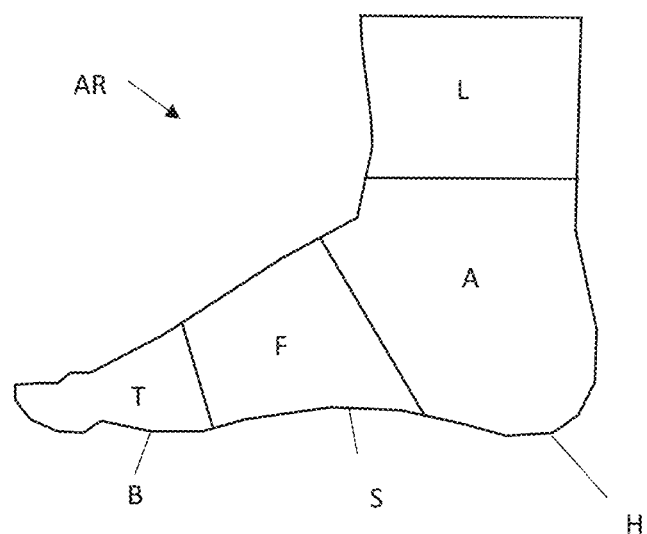
FIG. 2c illustrates a side view of the ankle region separated into a leg area, an ankle area, a foot area and a toe area.

In the description below, the naming shown in FIG. 2c is used, where an ankle region AR is shown to comprise a foot area F, a leg area L and an ankle area A between the foot area F and the leg area L. The foot area F roughly corresponds to the metatarsals area MTA of FIGS. 2a and 2b. In addition, a toe area T is shown in FIG. 2c. In addition, the instep and arch of the foot area is indicated with arrows in FIG. 2a. The instep is commonly known as the middle part of the foot, where it curves upwards. The arch of the foot is commonly known as the curve under the foot, between the heel and balls.

Two other terms will be used in the description below. The term "medial side" is referring to the inner side of the foot or the side being closest to the other foot. The term "lateral side" is referring to the outer side of the foot or the side being furthest away from the other foot.

Figure 3:
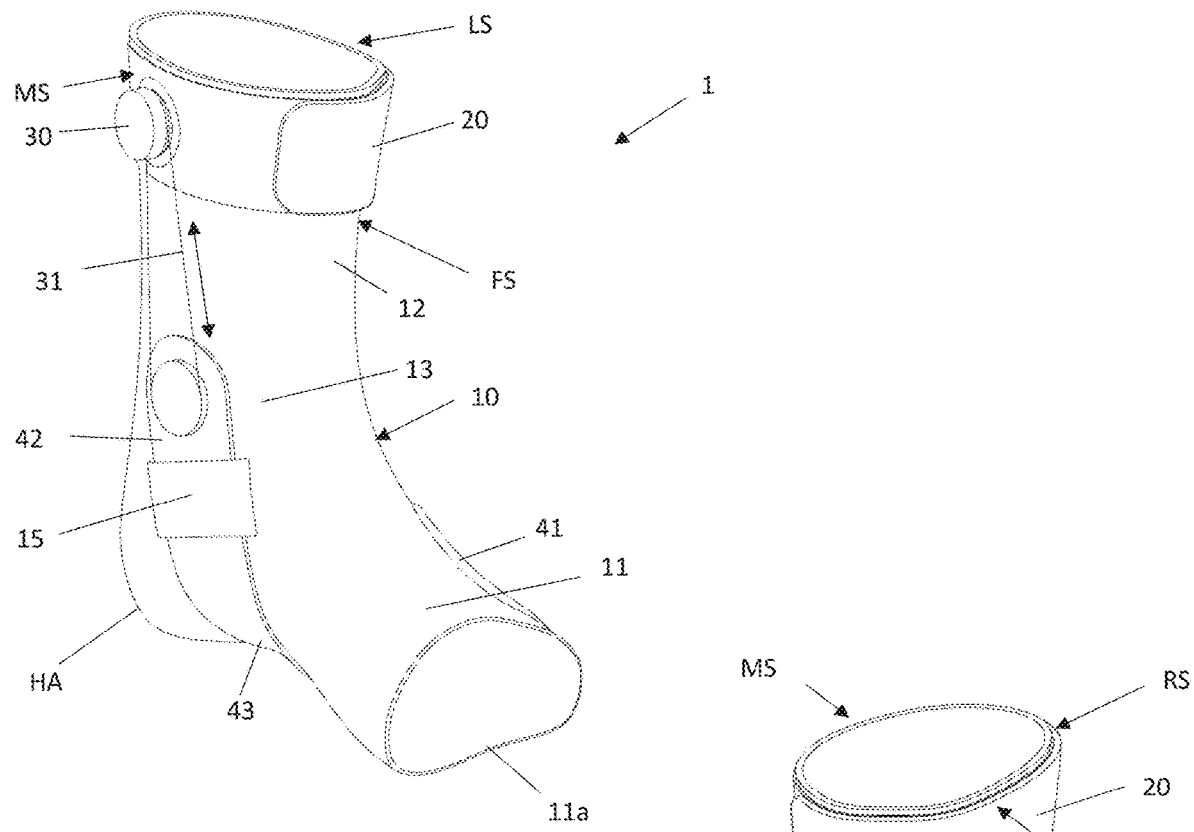
FIG. 3 illustrates a perspective front/medial view of a first embodiment.
Figure 4:
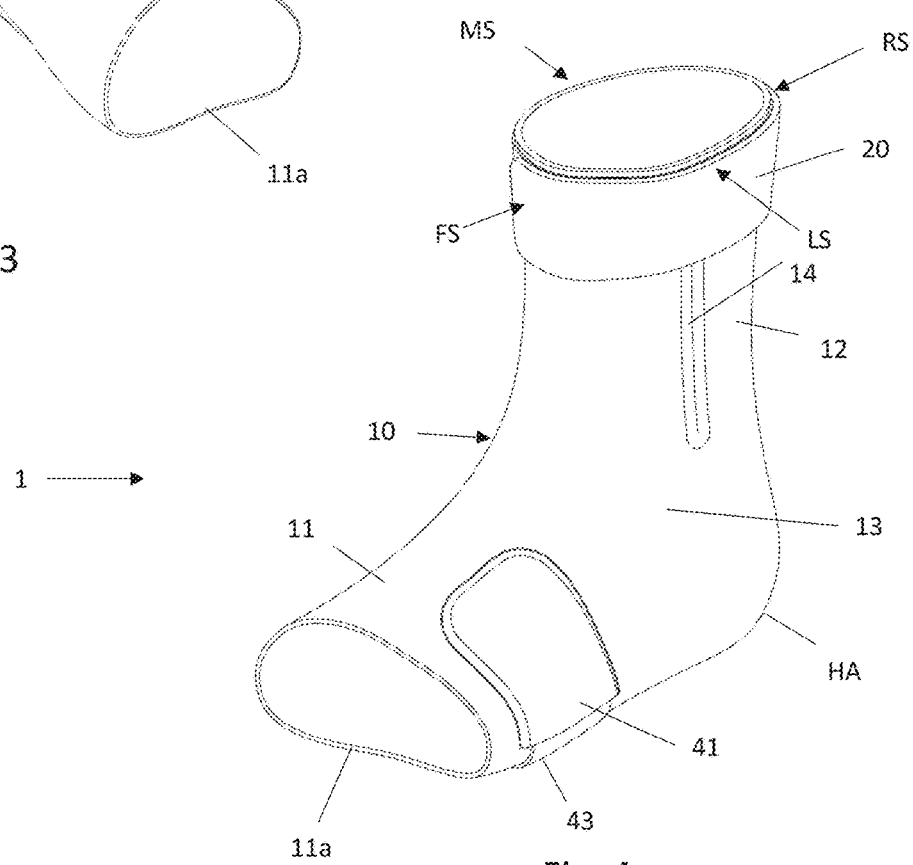
FIG. 4 illustrates a perspective front/lateral view of the first embodiment.

It is now referred to FIGS. 3, 4 and 5, where a first embodiment of a footwear 1 is shown. The footwear 1 comprises a sock body 10 comprising a foot section 11 for surrounding the foot area F, a leg section 12 for surrounding the leg area L and an ankle section 13 between the foot section F and the leg section L for surrounding the ankle area A. Parts of the underside of the foot section 11 is indicated as an arch section 11a. This is also shown in FIG. 6. In FIG. 6, it is also shown that the sock body 10 is not surrounding the toe region T.

When comparing FIG. 6 with FIGS. 2a and 2b, the foot section 11 of the sock body 10 is at least partially covering the metatarsal area MTA. Consequently, the foot section 11 of the sock body 10 is not covering the phalanges area PA.

The footwear 1 comprises a zipper 14 provided in the upper part of the leg section 12 of the sock body 10. By means of this zipper 14, it is easier for a user to put the sock body 10 on. In many cases, the ankle is swollen after an ankle sprain, in which case the zipper 14 is helpful. The zipper 14 also renders it possible to use a less elastic fabric than required if the zipper 14 was not present.

The footwear 1 further comprises a leg strap device 20. The leg strap device 20 comprises a band which can be tightened around the leg area L. The leg strap device 20 may comprise an elastic band or a non-elastic band. The leg strap device 20 may be fastened to the leg area L by means of a hook-and-loop fastener (Velcro®), or by a reel-based tensioning mechanism (Boa® Fit System). The leg strap device 20 may also comprise a friction increasing inner lining or coating, to prevent or reduce the risk of the leg strap device 20 sliding down along the leg of the user.

The footwear 1 further comprises an adjustable tensioning device 30 connected to the leg strap device 20. Preferably, the adjustable tensioning device 30 is connected on one of the sides of the leg strap device 20, i.e. a medial side (indicated as MS in FIGS. 3 and 4) or lateral side (indicated as LS in FIGS. 3 and 4), and not front or rear side.

It should be noted that from the shape of the sock body 10, the embodiment of the footwear 1 in FIGS. 3-5 is shown worn on the left foot of a user. Hence, the adjustable tensioning device 30 is here connected the medial side MS of the leg strap device 20. This will be discussed further in detail below.

The footwear 1 further comprises a tensioning element 40 having a first end section 41, a second end section 42 and an intermediate section 43 between the first and second end sections 41, 42.

The first end section 41 of the tensioning element 40 is connected to the foot section 11 of the sock body 10. The second end section 42 is connected to the adjustable tensioning device 30. The intermediate section 43 is provided below an arch section 11a of the foot section 11.

The tensioning element 40 of the adjustable tensioning device 30 is at least partially elastic. In the present embodiment, the entire tensioning element 40 is made of an elastic band having a width indicated in FIG. 5 as D40. The width D40 may be between 0.5-10 cm, preferably between 3-6 cm. However, it is possible that only the intermediate section 43 is made of an elastic band having such a width, while the first and second end sections 41, 42 are made of a non-elastic material. It should be noted that the elastic band has a certain width as described above to increase comfort for the user. If the width is too narrow or to wide, the intermediate section 43 may be uncomfortable to use, in particular when the footwear 1 is to be used inside a shoe.

In the present embodiment, the adjustable tensioning device 30 comprises a wire 31 connected to the second end section 42 of the tensioning element 40. The adjustable tensioning device 30 may be a reel-based tensioning device (for example the Boa® Fit System). Some of these reel-based tensioning devices are adjustable in one direction only, i.e. the tensioning adjusted continuous or stepwise, but to loosen the tensioning, the wire 31 must be fully released by pulling the reel. Preferably, the reel-based tensioning device is adjustable in both directions, i.e. the wire 31 can be tensioned and released in a continuous manner or stepwise manner by rotating the wheel in opposite directions. The wire 31 is preferably non-elastic.

As shown in the drawings, the entire tensioning element 40 is provided outside of the sock body 10, where the first end section 41 is adhered to the outside of the sock body 10. Alternatively, the intermediate section 43 may be integrated as part of the arch section 11a of the foot section 11 of the sock body 10. Also the connection of the first end section 41 to the foot section 11 of the sock body 10 may be done by incorporating the first end section 41 into the sock body 10.

In this embodiment, the leg strap device 20 is connected to the leg section 12 of the sock body 10 by means of a seam. Alternatively, an adhesive or other type of fasteners may be used. In yet an alternative, leg strap device 20 only connected to the sock body 10 by means of the tensioning element 40.

In the embodiment of FIGS. 3-5, the second end section 42 of the tensioning element 40 is provided at, or adjacent to the ankle section 13 of the sock body 10. In this embodiment, there is a distance between the second end section 42 and the leg strap device 20 due to the wire 31 of the adjustable tensioning device 30.

In FIGS. 3 and 5 it is shown that the footwear 1 further comprises a guide 15 connected to the ankle section 13 of the sock body 10 for positioning the tensioning element 40 in relation to the sock body 10.

Technical Function of Footwear

The technical function of the footwear 1 will now be described.

Initially, it should be noted that the main purpose of the leg strap device 20 is to hold the adjustable tensioning device 30 stationary with respect to the leg area L. Moreover, one important purpose with the sock body 10 is to keep the first end section 41 of the tensioning element 40, i.e. the area where the first end section 41 is connected to the sock body 10, stationary with respect to the foot area F.

As described above, the adjustable tensioning device 30 provides adjustable tensioning of the tensioning element 40 with respect to the foot section 11 of the sock body 10. As the adjustable tensioning device 30 is stationary or fixed in position with respect to the leg strap device 20, the adjustable tensioning device 30 provides adjustable tensioning of the tensioning element 40 between the foot section 11 of the sock body 10 and the leg strap device 20.

It is now referred to FIGS. 6a and 6b, where the technical effect of the footwear 1 is illustrated. The sock body 10 is here removed, while other parts of the footwear 1 is indicated schematically. It should be noted that parts of the tensioning element 40 are indicated with dashed lines—this is done to illustrate that these parts of the tensioning element 40 are provided below the foot and would normally not be visible in a front view such as FIGS. 6a and 6b.

In FIGS. 6a and 6b, the right foot is disclosed in two different positions. In FIG. 6a, the adjustable tensioning device 30 is provided on the medial side MS and the first end section 41 is connected on the opposite side, i.e. the lateral side. When tensioning the adjustable tensioning device 30, the foot area F is applied with a so-called inversion force IF. This inversion force IF forces the foot section to the position of FIG. 6a. Muscles in the ankle region AR must be actively used to counteract this inversion force IF to hold the foot in a "normal" position.

In FIG. 6b, the adjustable tensioning device 30 is provided on the lateral side LS and the first end section 41 is connected on the opposite side, i.e. the medial side. When tensioning the adjustable tensioning device 30, the foot area F is applied with a so-called eversion force EF. This eversion force EF forces the foot area to the position of FIG. 6b. Muscles in the ankle region AR must be actively used to counteract this eversion force EF to hold the foot in a "normal" position.

A "normal" position is here referring to a position between the positions of FIGS. 6a and 6b, and/or positions used by the user during walking, standing etc.

As described above, the sock body 10 is not surrounding the toe area T. Hence, the footwear 1 used on a right foot in FIG. 6a to provide an inversion force IF, may be used to provide an eversion force EF on a left foot as shown in FIG. 6c. I similar way, the footwear 1 used on a right foot in FIG. 6b to provide an eversion force IF, may be used to provide an inversion force IF on a left foot as shown in FIG. 6d.

Alternative Embodiments

Some alternative embodiments will be described below.

First, it is now referred to FIG. 8. Here it is shown an alternative embodiment where the foot section 11 may comprise a toe section 18. The toe section 18 may be elastic or adjustable, to achieve that the sock body 10 may be used on feet with different sizes.

It is now referred to FIG. 9. Here it is shown an alternative embodiment, where the adjustable tensioning device 30 comprises a hook-and-loop (Velcro®) type of fastener, where hooks are provided outside of the leg strap device 20 and loops are provided on the inside of the second end section 42 or vice versa. Here, the second end section 42 is provided in the leg area L, i.e. above the ankle area A.

In yet an alternative (not shown) the adjustable tensioning device 30 may be a buckle, a strap adjuster etc.

According to the above, the footwear 1 may be used for preventive training to avoid an ankle sprain by compensating for or counteracting the eversion force and inversion force.

In a first period of time after an ankle sprain, the above prior art AirCast/AirSelect is typically used to stabilize the ankle. Then, after this first period, the footwear 1 is used for rehabilitation by gradually train the muscles in the foot by compensating for or counteracting the eversion force and inversion force.

What is claimed is:

1. A footwear for rehabilitation after an ankle sprain or for preventive training to avoid an ankle sprain, wherein the footwear comprises:
    a sock body comprising a foot section, a leg section, and an ankle section between the foot section and the leg section, the foot section comprising an arch section;
    a leg strap device;
    an adjustable tensioning device directly connected on at least one medial side of the leg strap device;
    a tensioning element having a first end section, a second end section, and an intermediate section between the first and second end sections; and
    a guide directly connected to the ankle section of the sock body for positioning the tensioning element in relation to the sock body, wherein the tensioning element is disposed between the guide and the sock body;
    wherein the first end section of the tensioning element is connected to the foot section on the opposite side to the adjustable tensioning device, the second end section of the tensioning element is connected to the adjustable tensioning device, and the intermediate section of the tensioning element is provided below the arch section or integrated as part of the arch section such that the adjustable tensioning device and the tensioning element are configured to provide an adjustable inversion force by adjustment of the adjustable tensioning device; and
    wherein the adjustable tensioning device and the tensioning element are configured such that the adjustable inversion force forces the foot section towards an inverted position.

2. The footwear according to claim 1, wherein the adjustable tensioning device provides adjustable tensioning of the tensioning element with respect to the foot section of the sock body.

3. The footwear according to claim 1, wherein the tensioning element is at least partially elastic.

4. The footwear according to claim 1, wherein the second end section of the tensioning element is provided at, or adjacent to, the ankle section of the sock body or at, or adjacent to, the leg section of the sock body.

5. The footwear according to claim 1, wherein the leg strap device is connected to the leg section of the sock body.

6. The footwear according to claim 1, wherein the footwear comprises a zipper provided in an upper part of the leg section of the sock body.

7. The footwear according to claim 1, wherein the adjustable tensioning device comprises a reel-based tensioning mechanism.

8. A method for rehabilitation of an ankle region after an ankle sprain or for preventive training of an ankle region to avoid an ankle sprain, wherein the method comprises:
    putting a sock body of a footwear on to the ankle region, wherein the sock body comprises a foot section, a leg section, and an ankle section between the foot section and the leg section, the foot section comprising an arch section; wherein the footwear further comprises:
    a leg strap device;
    an adjustable tensioning device directly connected on at least one side of the leg strap device;
    a tensioning element having a first end section, a second end section, and an intermediate section between the first and second end section; and
    a guide directly connected to the ankle section of the sock body for positioning the tensioning element in relation to the sock body, wherein the tensioning element is disposed between the guide and the sock body;
    wherein the adjustable tensioning device is connected on a medial side of the leg strap device, the first end section of the tensioning element is connected to the foot section on the opposite side of the adjustable tensioning device, the second end section of the tensioning element is connected to the adjustable tensioning device, and the intermediate section of the tensioning element is provided below, or integrated as part of, the arch section;
    tightening the leg strap device of the footwear around a leg area;
    adjusting the adjustable tensioning device, resulting in an adjustable inversion force that forces the foot section towards an inverted position; and
    using muscles in the ankle region to counteract the inversion force.

* * * * *